(12) United States Patent
Howard et al.

(10) Patent No.: US 6,250,130 B1
(45) Date of Patent: *Jun. 26, 2001

(54) METHOD AND APPARATUS FOR MONITORING AN ASPIRATING AND DISPENSING SYSTEM

(75) Inventors: David J. Howard, Oberlin; Kurukundi Ramesh Murthy, Fairview Park; Ying Cha, North Olmsted, all of OH (US)

(73) Assignee: Bayer Corporation, Tarrytown, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/111,087

(22) Filed: Jul. 6, 1998

Related U.S. Application Data

(63) Continuation-in-part of application No. 08/826,330, filed on Mar. 27, 1997, now Pat. No. 5,777,221, which is a continuation of application No. 08/499,820, filed on Jul. 10, 1995, now abandoned.

(51) Int. Cl.[7] .................................................. G01F 25/00
(52) U.S. Cl. .............................. 73/1.36; 73/168; 73/1.16
(58) Field of Search .......................... 73/1.36, 168, 1.16, 73/1.27, 1.28

(56) References Cited

U.S. PATENT DOCUMENTS

| | | | |
|---|---|---|---|
| 4,011,459 | 3/1977 | Knollenberg et al. | 73/865.5 |
| 4,331,262 | * 5/1982 | Snyder et al. | 73/1.36 |
| 4,366,384 | 12/1982 | Jensen | 250/577 |
| 4,384,578 | 5/1983 | Winkler | 604/114 |
| 4,399,711 | 8/1983 | Klein | 250/577 |
| 4,517,302 | 5/1985 | Saros | 73/864.22 |
| 4,705,668 | * 11/1987 | Kaltenbach et al. | 422/82 |
| 4,816,695 | 3/1989 | Lavin | 250/573 |
| 4,821,586 | * 4/1989 | Scordato et al. | 73/864.18 |

(List continued on next page.)

FOREIGN PATENT DOCUMENTS

| | | | |
|---|---|---|---|
| 0109198 | 5/1984 | (EP) . | |
| 0416808 | 3/1991 | (EP) . | |
| 0753721 | 1/1997 | (EP) | G01F/13/00 |
| 2106670 | 4/1983 | (GB) . | |

OTHER PUBLICATIONS

"CCD 800 Series Service Manual" for the Ciba Corning 800 Series Blood Gas Instrument (1994).

*Primary Examiner*—Hezron Williams
*Assistant Examiner*—Nashmiya Fayyaz
(74) *Attorney, Agent, or Firm*—Weingarten, Schurgin, Gagnebin & Hayes LLP

(57) ABSTRACT

A pump system and method for controlling and monitoring the aspiration of a liquid and the subsequent dispense of the liquid. As a pump is operated to either aspirate or dispense a liquid, a processor circuit receives input from a liquid air detector to sample the detected conditions in relation to the operation of the pump. In one embodiment, the pump employs a stepper motor, and the processor records information regarding the detected contents of the pathway at intervals correlating to the motor activity. A profile of detector output versus motor intervals is thus created from the point an aspiration cycle is commenced at least until a fluid-to-air boundary is detected, or from the point a dispense cycle is commenced, through an air-to-fluid boundary. Each profile is then compared against a standardized profile to determine if the detected transition occurred at a desired point in the profile. The processor circuit is programmable to define acceptable margins of error relative to the reference profile, and to define a variety of error conditions.

6 Claims, 11 Drawing Sheets

U.S. PATENT DOCUMENTS

| | | | |
|---|---|---|---|
| 4,844,887 | 7/1989 | Galle et al. | 422/65 |
| 4,896,270 * | 1/1990 | Kalmakis et al. | 73/864.16 |
| 4,897,797 | 1/1990 | Free, Jr. et al. | 364/500 |
| 4,931,774 | 6/1990 | Bachman | 250/577 |
| 5,131,591 * | 7/1992 | Gill | 73/1.36 |
| 5,183,765 | 2/1993 | Qureshi et al. | 436/180 |
| 5,211,626 | 5/1993 | Frank et al. | 604/65 |
| 5,271,902 | 12/1993 | Sakka et al. | 73/863.01 |
| 5,447,692 | 9/1995 | Keenan et al. | 422/116 |
| 5,463,228 | 10/1995 | Krause | 250/577 |
| 5,724,142 | 3/1998 | Kaminski et al. | 356/379 |
| 5,929,314 * | 7/1999 | Bergkvist et al. | 73/1.36 |

* cited by examiner

METHOD AND APPARATUS FOR MONITORING AN ASPIRATING AND DISPENSING SYSTEM

CROSS-REFERENCE TO RELATED APPLICATIONS

This application is a continuation-in-part of U.S. patent application Ser. No. 08/826,330, filed Mar. 27, 1997, now U.S. Pat. No. 5,777,221 which is a continuation of U.S. patent application Ser. No. 08/499,820, filed Jul. 10, 1995, now abandoned.

FIELD OF THE INVENTION

The present invention relates to optical flow verification systems, and in particular to an optical flow verification system employing reflectivity measurements to confirm aspiration or dispense of a liquid volume.

BACKGROUND OF THE INVENTION

Medical laboratories increasingly rely upon automated assay equipment in order to handle large numbers of assays efficiently in terms of time and cost, and further to increase the reliability of such assays by decreasing the amount of human intervention involved in such assays. However, this reduction in human intervention necessitates a corresponding increase in equipment and devices which ensure the accurate performance of such automated assays. In particular, regulatory agencies responsible for oversight of such testing are reluctant to approve certain forms of automated equipment absent enhanced monitoring and error reporting devices.

Assay equipment currently in use is commonly programmed for withdrawal of a desired reagent in preparation for execution of an assay. While such programmed aspirations are typically accurate, there remains the possibility that a reagent source has run dry though the assay equipment continues to aspirate from the empty reagent container, giving a "short shot" of reagent. Further, while an initial indication that reagent exists in a respective container prior to aspiration may be provided, equipment does not currently detect the evacuation of a supply of reagent during an aspiration. Finally, reagent aspiration equipment in existing automated assay apparatus does not provide the capability to detect an occlusion or an incorrect flow rate in real time or errors from a line break.

Optical verification systems are presently used to measure the transmittance of light through a tube as affected by the contents of the tube. Such transmittance detectors include a light source disposed opposite a light sensor on either side of a tube and are primarily useful for detecting and identifying the contents of a tube at any given moment, and do not find utility in confirming a volume of aspirated liquid.

SUMMARY OF THE INVENTION

The present invention provides an apparatus for verifying a volume of reagent aspirated within an automated assay instrument. A tube has a reagent probe disposed at one end, and a pump or like device disposed at an opposite end. Intermediate the probe and the pump is an optical fluid detector having a housing, through which a transparent portion of the tube passes. Within the fluid detector housing, the fluid detector includes an optical source, such as an infra-red light emitting diode, disposed proximate the tube and oriented to illuminate the interior of the tube. The fluid detector also includes, within the housing and proximate the tube passing therethrough, a photodetector, oriented ninety degrees about the circumference of the tube to detect optical source illumination reflected off an interior surface of the tube opposite the optical source.

The photodetector provides one voltage level when a gas is within the tube in the optical fluid detector, and a different voltage when a liquid is within the tube. This is due to the absolute differences between the refractive indexes of the content of the tube and the tube itself. A threshold determining and comparison circuit in communication with the detector discriminates between the two levels. The rate at which aspirate is pumped and the volume of the tube from a probe tip inlet to the detector are known, typically by using a stepper motor driven syringe plunger on the end of the tube. Therefore, a given volume of aspirate should take a predictable amount of time (or steps) to pass through the detector, taking into consideration established tolerances. Typically, the tube is water filled to the probe tip before aspiration. Time (or stepper motor steps) is measured from the start of the aspiration of reagent. A liquid-air transition is detected at the end of the aspiration of reagent occasioned by the tip being withdrawn from the reagent source and the pump being driven further to place the reagent in a heater zone. If the liquid-air transition is not seen at the expected time, one of several problems with the aspiration are assumed, and the assay is canceled.

A further embodiment of the presently disclosed invention utilizes essentially the same hardware as described in the foregoing, though the data processing which is performed on the output of the threshold determining and comparison circuit differs. For instance, in this further embodiment, a processor circuit receives input from both the threshold determining and comparison circuit and a pump control circuit for the purpose of sampling the detected conditions at the photodetector in relation to the operation of the pump. A profile of photodetector condition versus pump operation is thus created from the point an aspiration cycle is commenced at least until a fluid-to-air boundary is detected, or from the point a dispense cycle is commenced at least until an air-to-fluid boundary is detected. Each profile is then compared against a standardized profile in order to determine if the detected transition occurred at a desired point in the profile.

The processor circuit is programmable to define acceptable margins of error relative to the reference profile, and to define a variety of error conditions under which the detected profile is designated as being outside of an acceptable range. For instance, a maximum number of fluid-air or air-fluid boundaries may be defined, above which the aspirate or dispense function is flagged as in error, and suitable warning, maintenance or diagnostics routines are initiated.

It is an object of the present invention to provide to an automated assay instrument offering an enhanced measure of confidence in the withdrawal accuracy of a desired quantity of aspirate. It is a further object of the present invention to provide error detection and notification which is applicable to a variety of error conditions.

BRIEF DESCRIPTION OF THE DRAWINGS

These and other features of the present invention are more fully set forth below in the fully exemplary detailed description and accompanying drawings of which.

DETAILED DESCRIPTION

Figure 1:
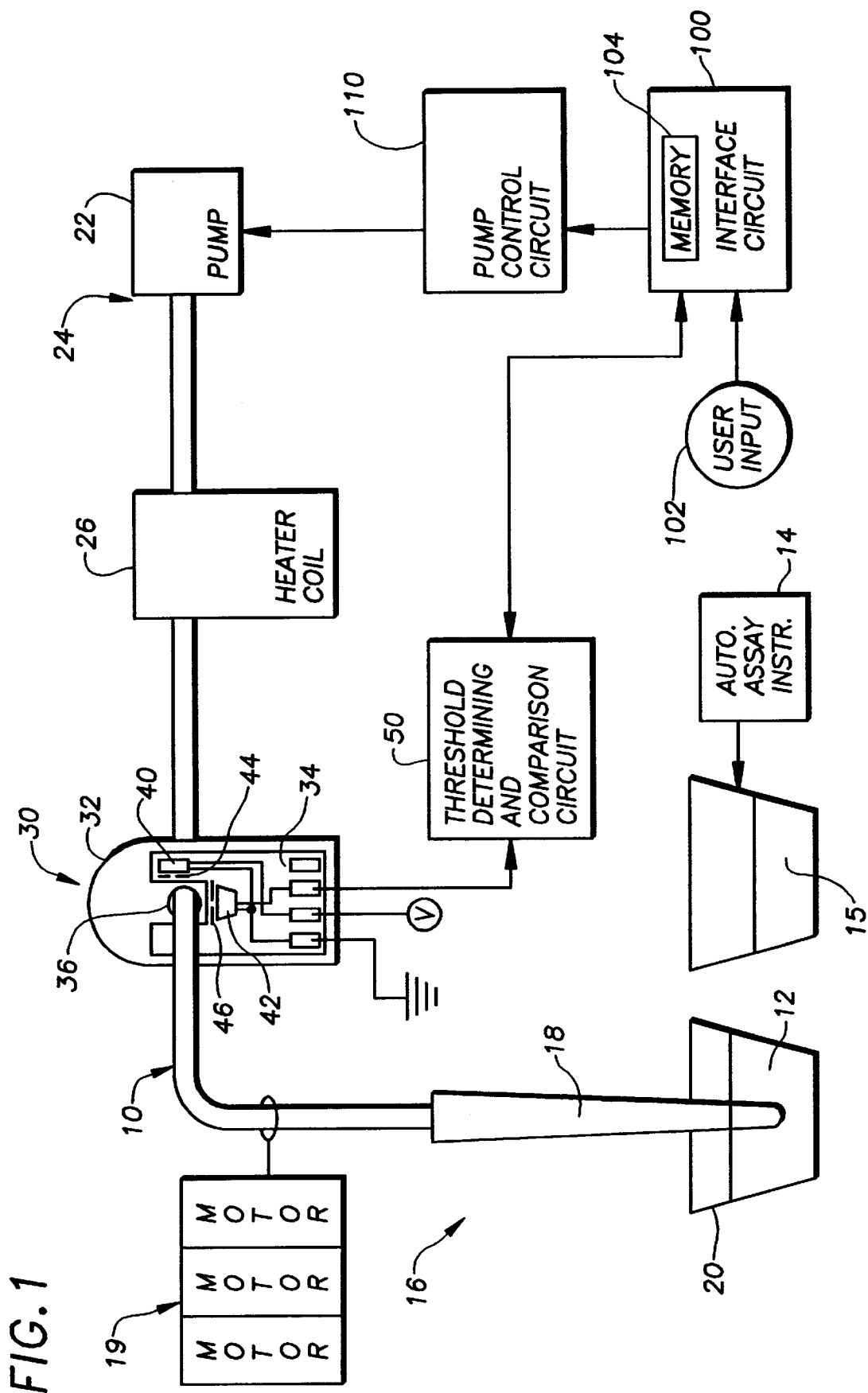
FIG. 1 is a schematic view of elements comprising a volume detection apparatus according to the present invention.

Various components of the volume detection apparatus according to the present invention are illustrated in FIG. 1. In particular, a tube 10 provides aspirate 12 such as a reagent for sample 15 dilution at a station within an automated assay instrument 14 from a reagent container 20. A probe 18 is connected to a first end 16 of the tube 10 for withdrawal of reagent 12 from the container 20 and into the tube 10. In a preferred embodiment, the probe 18 is manipulated automatically by one or more motors 19 such as stepper motors to aspirate from the reagent container 20 and dispense in the sample container 15. These motors translate the probe from one container to another.

To withdraw reagent into the tube, a pump 22 is disposed at a second end 24 of the tube 10. The pump 22 in one embodiment is a positive displacement pump such as a diluter or syringe pump.

Intermediate the tube first and second ends 16, 24, the illustrated embodiment includes a heater coil 26. In some situations, it is preferable to refrigerate reagents to maintain their efficacy. However, this necessitates the heating of the reagent prior to use in the automated assay instrument 14. Otherwise, the lowered temperature of the reagent may adversely affect the performance of an assay in which it is used.

Also disposed intermediate the first and second ends 16, 24 of the tube 10 is an optical fluid detector 30 having a housing 32. The tube 10 passes through an orifice 36 in the housing 32 so that the tube 10 is generally normal to a plane defined by the housing 32. For the purposes of illustration, a cover of the housing 32 has been removed. A circuit board 34 disposed within the housing 32 provides a mounting surface for an optical source 40 and a photodetector 42 disposed adjacent the tube 10.

In a first embodiment, the optical source 40 is a light emitting diode (LED) generating infrared illumination. In a further embodiment, the optical source 40 is fabricated directly on the circuit board 34 as an integrated device. Power and ground leads are further provided on the circuit board 34 in communication with the optical source 40.

The optical source 40 is provided with a narrow width slit aperture 44, parallel to the tube 10. This aperture 44 allows IR illumination to enter the tube 10 in a narrow dispersion pattern. Preferably, the housing 32 and associated tube 10 support elements integral to the housing 32 and adjacent to the optical source 40 and photodetector 42 are formed of a material opaque to visible light, but transparent to IR illumination. This avoids spurious readings due to ambient illumination entering the photodetector 42.

The photodetector 42 is similarly disposed on the circuit card 34 adjacent the tube 10, though the photodetector 42 is located ninety degrees about the circumference of the tube 10 from the optical source 40. Similar to the optical source 40, the photodetector 42 is provided with a small width slit aperture. Thus, the photodetector 42 is particularly sensitive to IR light reflected off the interior wall of the tube 10, which varies with the reflective index of the contents of the tube 10. The photodetector 42 is therefore provided as a reflectivity sensor as contrasted with a turbidity sensor which detects light scattered by the contents of the tube 10.

In summary, light from the optical source 40 illuminates the interior of the tube 10. A portion of this light is reflected off an inner wall of the tube 10 to a degree determined by the respective reflective indexes of the tube and the contents of the tube and is detected by the photodetector 42. The photodetector 42 detects a smaller amount of reflected light when there is liquid within the tube 10 in front of the optical source 40 and photodetector 42 as compared to when a gas such as ambient air is within the tube 10. The respective apertures 44, 46 enhance the sensitivity of the apparatus such that air bubbles of a few microliters are detectable.

The photodetector 42 of the present invention is interfaced to a circuit 50 labeled "Threshold Determining and Comparison Circuit". This circuit, which is illustrated in detail in FIG. 2, establishes a reference voltage level against which signals from the photodetector 42 are compared to establish when liquid versus air is within the tube adjacent the photodetector 42.

Figure 2:
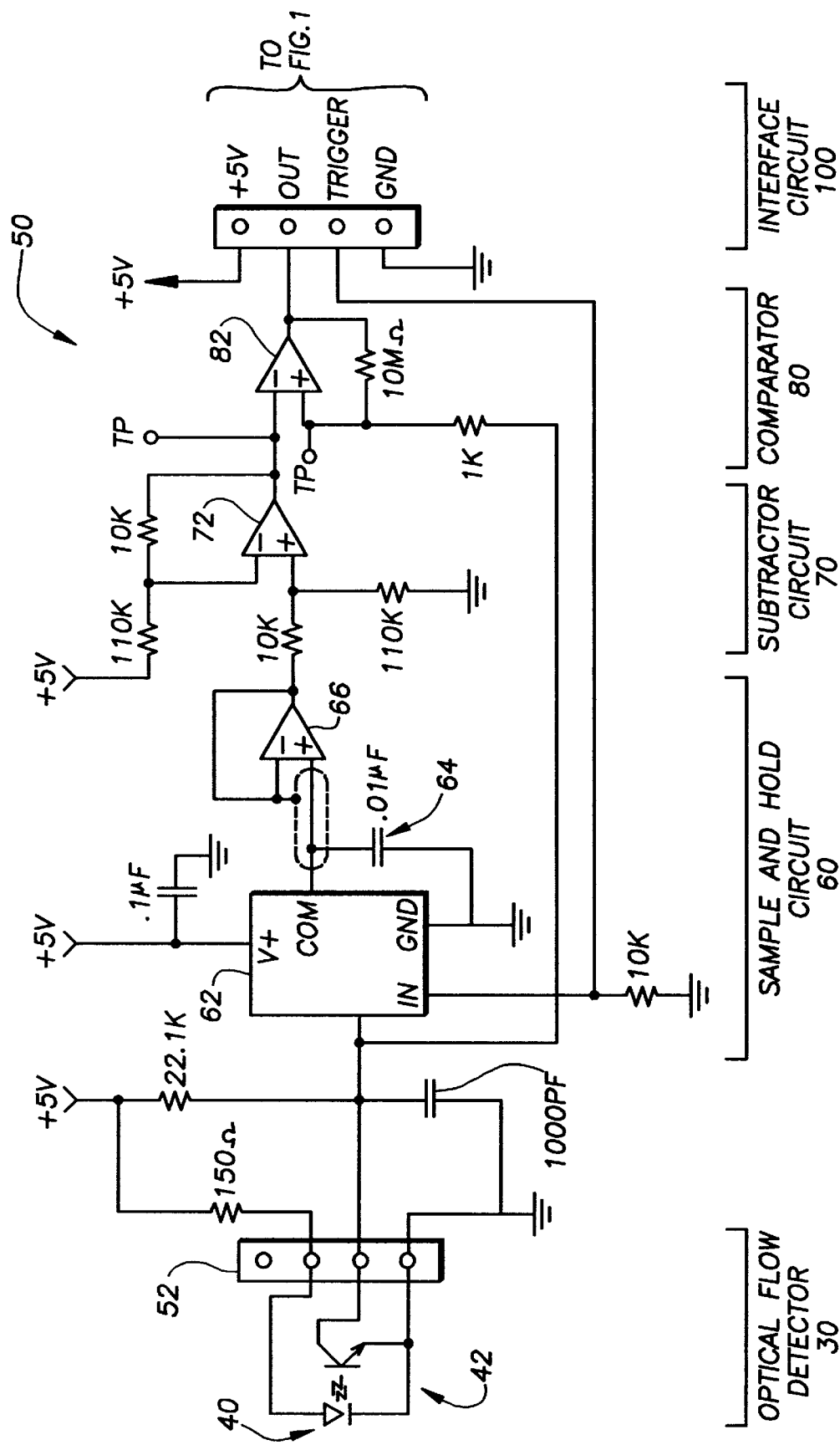
FIG. 2 is a schematic view of a threshold determining and comparison circuit as employed in the apparatus of FIG. 1.

With reference now to FIG. 2, the threshold determining and comparison circuit 50 includes a connection interface 52 to the optical fluid detector 30. Power and a ground reference are provided to the fluid detector 30. A signal from the photodetector 42, representative of the quantity of light reflected to the photodetector 42, is provided to a sample and hold circuit 60. Included within this circuit 60 is an analog switch 62, in one embodiment a "MAX323CSA" manufactured by Maxim Integrated Products of Sunnyvale, Calif. U.S.A. The switch 62 is utilized by connecting the photodetector 42 output to a normally open (NO) input terminal of the switch 62. A trigger signal, provided from an interface circuit 100 (to be described subsequently), is connected to a logic input (IN) terminal of switch 62 to control the operation of the switch 62. In one logic state, the photodetector output is connected through the normally open terminal to a common terminal (COM). In another state, the photodetector 42 signal is disconnected from the COM output while its last value is held by capacitor 64. This results in the sample and hold circuit 60 latching onto a voltage level coming from the photodetector 42. The op-amp 66 receives this signal as a buffer amp for preventing leakage of the sample and hold output.

The output of the buffer 66 is provided to a subtractor circuit 70 which includes an op-amp 72 configured to subtract 0.45 V from the output of the sample and hold circuit 60 and to provide the result as a reference voltage ($V_{ref}$).

Finally, the threshold determining and comparison circuit 50 includes a comparator 80 including an op-amp 82 configured to compare the output from the photodetector 42 with the reference voltage from the subtractor circuit op-amp 72. The result is then provided as an output from the threshold determining and comparison circuit 50 and as an input to the interface circuit 100.

With reference to FIG. 1, the interface circuit 100 receives user input from a source 102, including the expected volume of reagent to be aspirated. The interface circuit 100 further comprises a memory 104 for storing information such as the known volume of the probe 18 with the tube 10 up to the optical fluid detector 30, as well as the rate at which the pump 22 withdraws reagent into the probe 18 and tube 10. With volume and rate known, the expected time for a reagent aspiration to pass by the detector 30 is calculated. Output from the threshold determining and comparison circuit 50 is checked (as described later) to verify that the aspiration indeed takes the expected amount of time within some tolerance. If not, a malfunction in the aspirate withdrawal system is indicated and the system can react accordingly, as by the cancellation of further reagent aspirations, the notification of a user of the error condition, and the initiation of diagnostic measures.

The interface circuit 100 also provides commands to a pump control circuit 110 based upon the user input from source 102. Such input in one embodiment includes pump on and off signals in the form of a command to begin an assay. In an alternative embodiment, such input includes pump rate information. In the latter embodiment, the variable rate is factored into the elapsed time calculations carried out by the interface circuit 100.

The generation of various signals from the photodetector 42 output and their use in the threshold determining and comparison and interface circuits 50, 100 are now described with reference to FIGS. 3 through 5. Here, only the tube 10, the probe 18, the optical fluid detector 30 (with a cover attached), and the reagent container 20 are carried over from FIG. 1 for the sake of simplicity. As previously noted, the interface circuit 100 has stored therein the known volume of the probe 18 and tube 10 from a distal end of the probe 18 to the optical fluid detector 30, as well as the rate at which the pump 22 draws air and liquid through the tube 10. Therefore, the elapsed time required to aspirate a certain volume of reagent through the probe 18 and tube 10 to the fluid detector 30 can be calculated.

The presently disclosed invention provides an indication of the actual elapsed time in the following manner. The presently disclosed apparatus is a water-backed system, meaning that the probe 18 and tube 10 are filled with water up to a region, for example, 28 when not conveying reagent or air. In a first embodiment, water is provided by automatically manipulating the probe 18 into a water-filled container 120 and activating the pump 22, thus drawing water 28 into the probe 18 and tube 10. In a second embodiment, water is provided within the tube 10 by operation of one or more valves connecting the tube 10 to another water-filled container (not illustrated).

Figure 6:
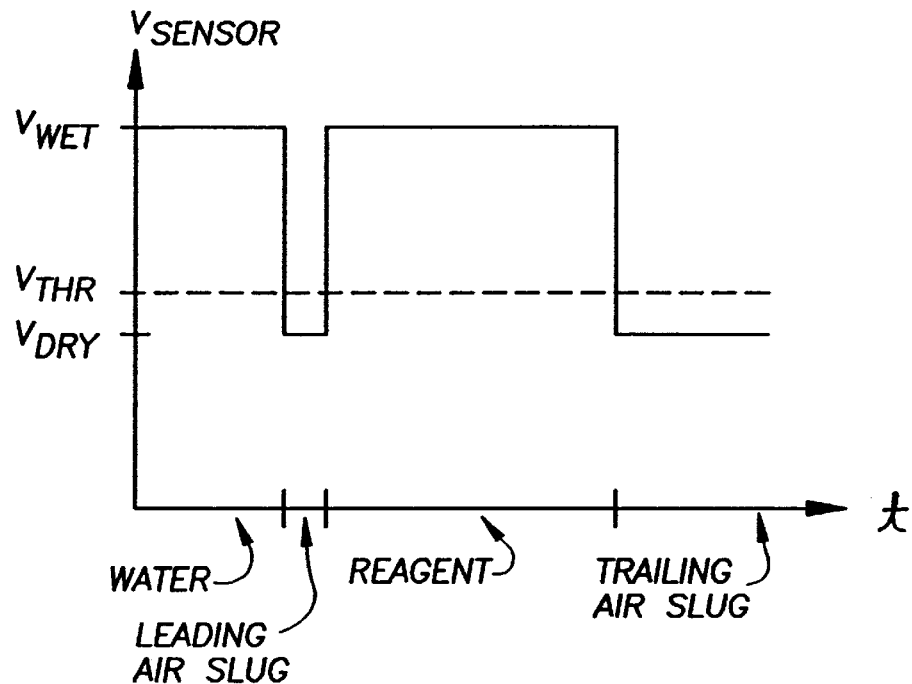
FIG. 6 is a graph illustrating the relative amplitude and timing of signals employed in the detection apparatus of FIG. 1.

Light is less readily reflected within the tube 10 when it is filled with a liquid. Therefore, a higher voltage level ($V_{wet}$) is returned by the photodetector 42 to the sample and hold circuit 60 when liquid is in the tube 10 than when air is within the tube 10 ($V_{dry}$), as illustrated in FIG. 6. With water throughout the tube 10, and in particular within the optical fluid detector 30, the interface circuit sends a trigger signal to the threshold determining and comparison circuit 50. As previously noted with respect to FIG. 2, the trigger signal causes the sample and hold circuit 60 to hold the current voltage level ($V_{photo}$) from the photodetector 42. This level is then subject to the subtractor circuit 70.

The goal is to compare a returned voltage from the photodetector 42 ($V_{photo}$) to a reference voltage ($V_{ref}$) in order to determine whether air or liquid is before the photodetector 42 at that moment. To make the present optical fluid detector 42 independent of the unique characteristics of each particular optical fluid detector 30 ($V_{wet}$ and $V_{dry}$ may not be the same for each detector), a threshold level is chosen slightly above the maximum returned voltage level when air is within the tube at the photodetector 42 ($V_{dry}$).

Since the difference between wet ($V_{wet}$) and dry ($V_{dry}$) voltages does not fall below 0.5 V in any optical fluid detector 30, regardless of absolute values, the voltage threshold ($V_{thr}$) (above which is always $V_{wet}$ and below which is always $V_{dry}$) is chosen as $V_{dry}$ minus a value slightly less than the difference between $V_{wet}$ and $V_{dry}$. In one embodiment, $V_{wet} - V_{dry} = 0.5$ V, so $V_{thr}$ is chosen as $V_{wet} - 0.45$ V. As such, the subtractor circuit 70 in this instance subtracts 0.45 V from $V_{wet}$ to form $V_{thr}$, $V_{wet}$ being determined by triggering the sample and hold circuit 60 when water is within the tube 10 at the optical fluid detector, such as immediately before the start of aspirating a reagent sample. Since $V_{wet} > V_{thr}$, the output of the comparator ($V_{out}$) 80 is "high". The threshold level relative to the absolute values of the photodetector is shown in FIG. 6. By relying upon a guaranteed minimum difference between $V_{wet}$ and $V_{dry}$ rather than on the absolute values of these measurements, the need to calibrate is eliminated.

Next, to provide an indication that a reagent volume is about to pass by the detector 30 within the tube, the probe 18 is withdrawn from all containers and the pump is activated for a relatively short period of time prior to withdrawing a quantity of reagent 12 into the tube 10. This causes a leading air slug 122 to be drawn into the probe 18 (FIGS. 3 and 4). However, the photodetector 42 will continue to sense liquid in the tube until the leading air slug 122 progresses through the tube 10 to the optical fluid detector 30.

Figure 4:
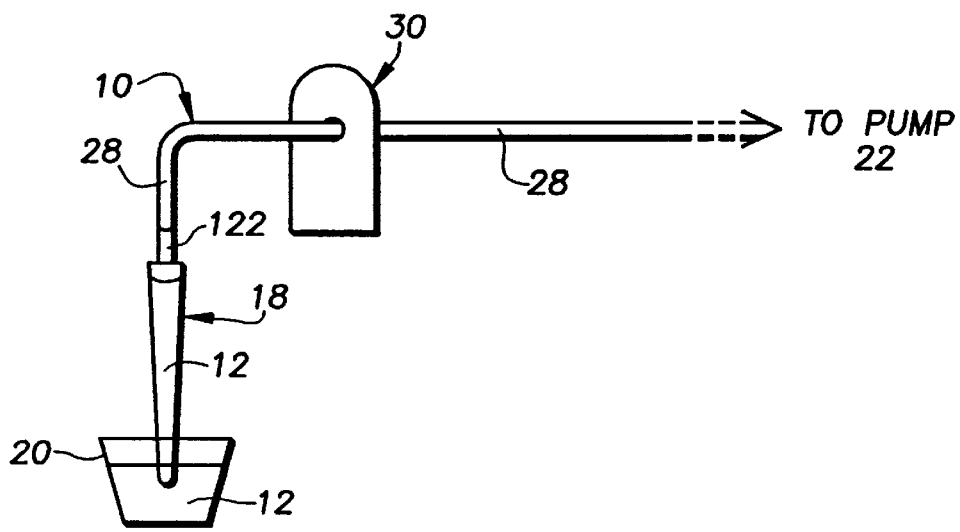

Next, as shown in FIG. 4, the probe 18 is manipulated into the reagent container 20 and the pump 22 is activated by the pump control circuit 110. Feedback circuitry (not illustrated) may be provided in a further embodiment in order to verify the physical disposition of the probe 18 within the reagent container 20. At this point, water remains in the majority of the fluid path, followed by the leading air slug 122 which is shown just emerging above the probe 18.

Figure 5:
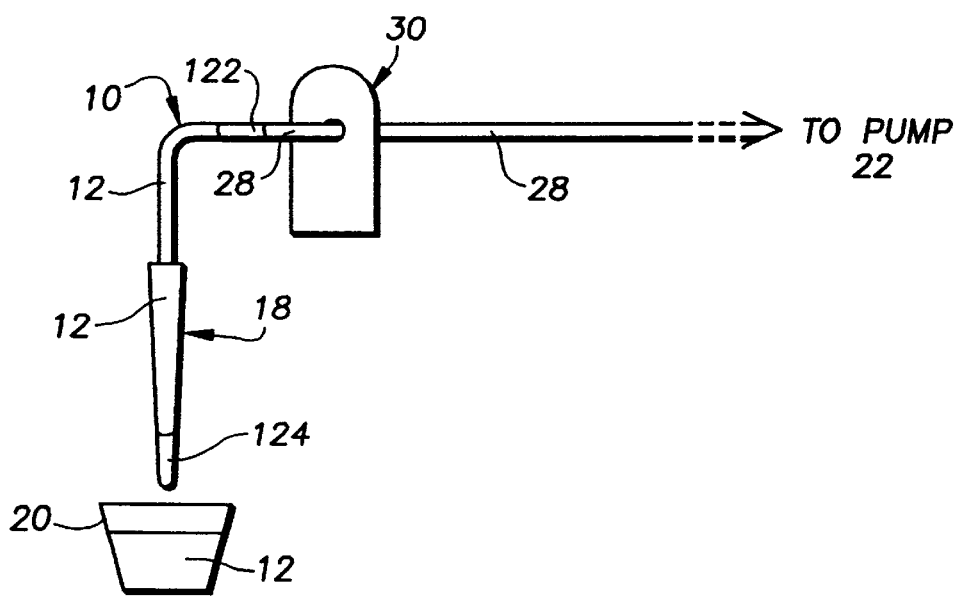
Figure 7:
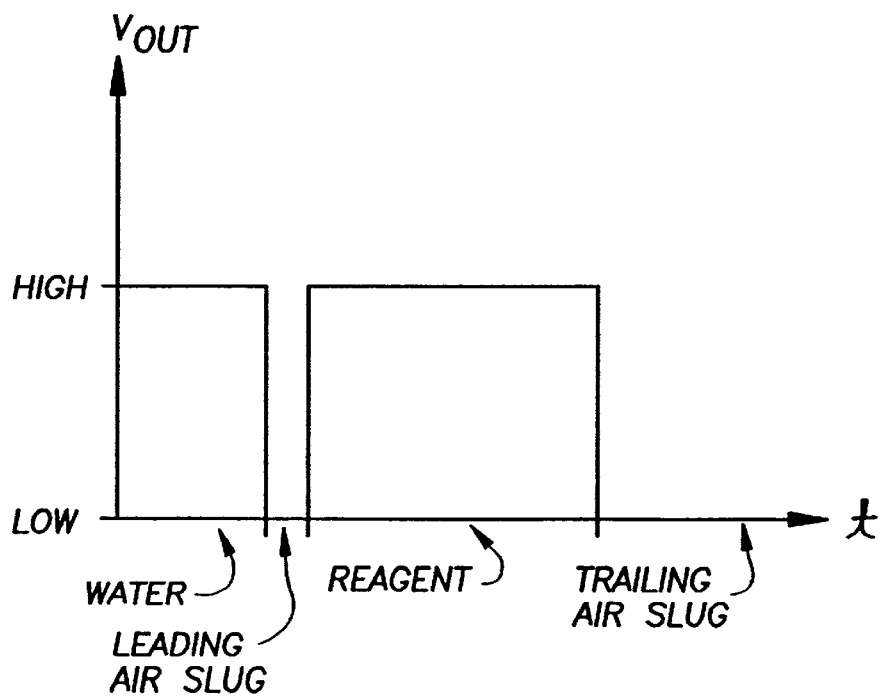
FIG. 7 is a graph illustrating the timing of signals employed in the detection apparatus of FIG. 1.

In FIG. 5, a quantity of reagent 12 has been withdrawn into the probe 18 and tube 10, and the probe 18 has been raised out of the reagent container 20. The pump 22 then draws a trailing air slug 124 into the probe 18 following the reagent 12 aspirate. As shown, the optical fluid detector 30 is typically, but not necessarily, still presented with water in the tube 10, and as such the photodetector voltage remains at $V_{wet}$, and the output of the comparator 80 ($V_{out}$) remains "high" as in FIG. 7.

Further activation of the pump 22 causes the leading air slug 122 to progress until it is at the optical source 40 and photodetector 42. At this point, the higher reflectivity of air is sensed by the photodetector 42, resulting in a "low" output ($V_{out}$) of the comparator circuit 80, as in FIG. 7. Firmware within the interface circuit 100 checks to see if $V_{out}$ remains "low" for a minimum period, corresponding to a minimum leading air slug 122 volume within the tube 10. If large enough, the firmware assumes this is the leading air slug 122 and begins counting on the next "low" to "high" transition of $V_{out}$, which corresponds to the detection of liquid (reagent) passing through the tube 10 before the photodetector 42.

If the air detected before the photodetector does not persist long enough (i.e. $V_{out}$="low" for too short a time), it is assumed that this air was an air bubble and not the leading air slug 122.

Once the leading air slug 122 has been identified, the interface circuit continues counting until a "high" to "low" transition is returned from the threshold determining and comparison circuit 50, corresponding to the passage of the trailing air interface 124 before the photodetector 42. The interface circuit 100 is provided with the desired reagent volume via the user interface 102 or via its own memory 104. In conjunction with known rate and volume information, the interface circuit 100 is capable of calculating the time in which the trailing air slug 124 should have been seen, within a given target range. The larger the removed volume, the larger the target range. The probe is then manipulated by motors 19 to a point where the reagent can be dispensed in a sample 15, or is conveyed within a system of valves and further tubes (not illustrated).

If the trailing air interface 124 is not seen within this range, the interface circuit 100 sends an indication of this state for use, for example, in halting all further assays using this reagent in particular or all reagents, and/or of notifying a user via a user interface. This error could occur due to a number of causes, including an empty reagent container 20, an occluded tube 10 or probe 18, and a failing or failed pump 22.

Figure 3:
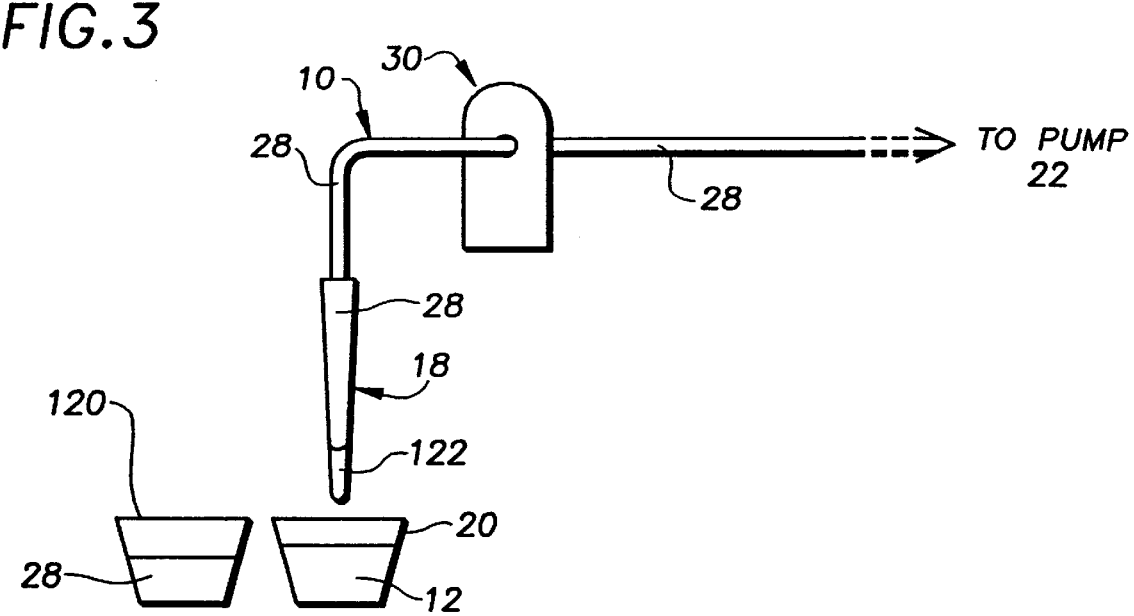
FIGS. 3 through 5 are simplified illustrations of the detection apparatus of FIG. 1 in various stages of aspirating a reagent sample.

In FIGS. 3 through 5, the volume of reagent aspirated was small enough so that both the leading and trailing air regions 122, 124 were within the tube 10 or probe 16 before the leading air slug 122 was within the optical fluid detector 30. In other instances, the leading air slug 122 is drawn within the optical fluid detector 30 while the probe 18 is still within the reagent container 20 and while the pump is still drawing reagent into the probe 18 and tube 10. This does not impact the ability of the threshold determining and comparison circuit 50 or the ability of the interface circuit 100 to count as the reagent 12 is drawn through the apparatus.

Having described preferred embodiments of the invention, it will now become apparent to one skilled in the art that other embodiments incorporating the concepts may be used.

Though the invention has been described as finding utility as part of an automated assay instrument requiring reagent, the presently disclosed invention can be utilized for the transfer of other liquids for other purposes.

Further, though a positive displacement pump such as a diluter is disclosed, other pumping devices can be used with the present invention such as dilutors. In fact, this verification system is particularly useful with pumps which are not as reliable in terms of accuracy of withdrawn liquid.

The tube of the present invention is formed of Teflon (E. I. du Pont de Nemours & Co., Inc., Wilmington, Del., U.S.A.), though other non-reactive, light transmissive materials can be used. The choice of frequency for the optical source 40 can also be varied depending upon the tube material and the contents to be sensed.

Figure 8:
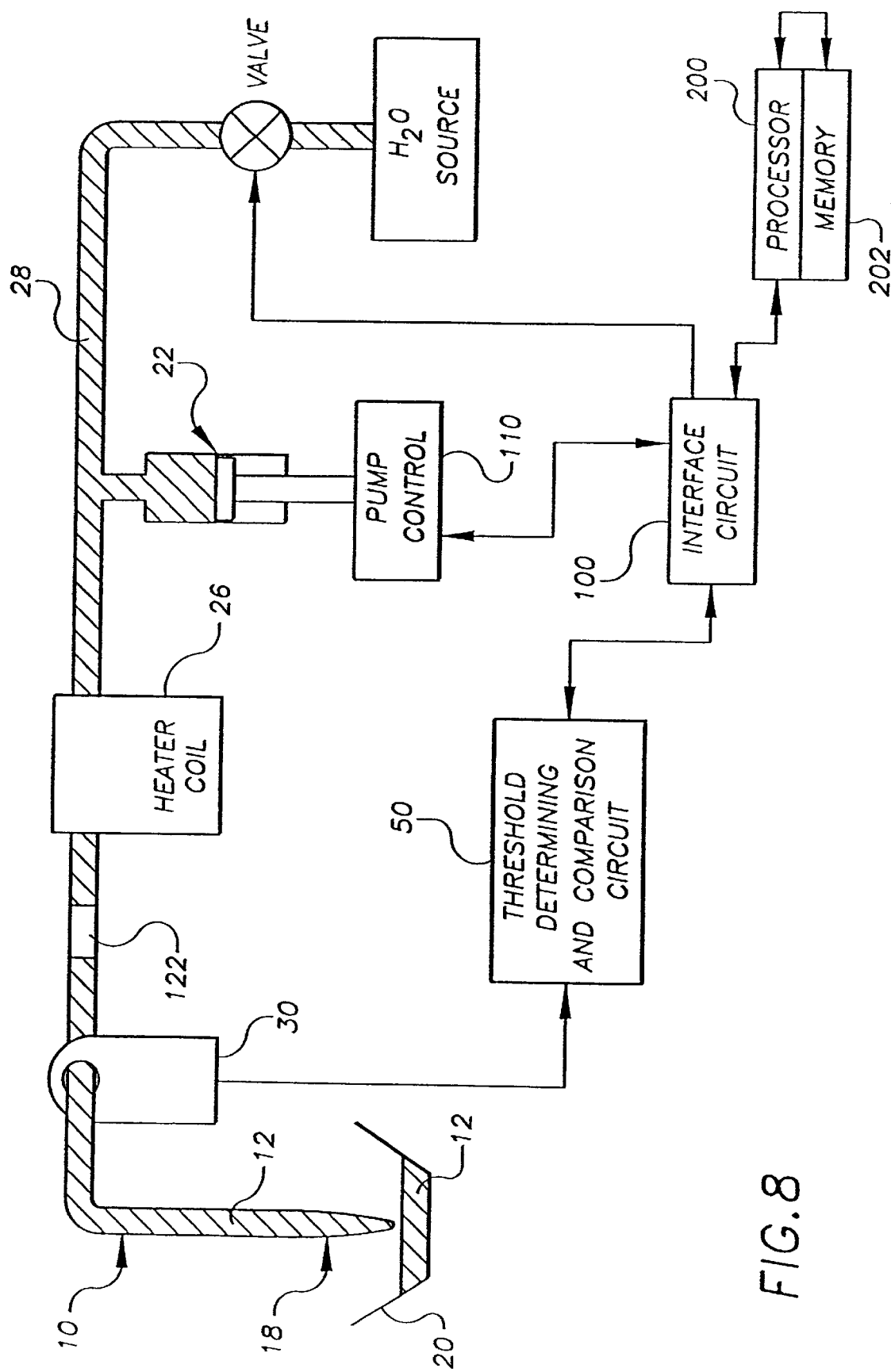
FIG. 8 is a schematic view of a further embodiment of the present invention utilized for monitoring aspirating and dispensing functions.

A further embodiment of the presently disclosed invention is illustrated in FIG. 8, where elements in common with the embodiment of FIG. 1 are identified by the same reference numerals. FIG. 8 includes a source of pressurized de-ionized water for priming the illustrated pump system. Such water backing can be employed in one embodiment of the system of FIG. 1 as well.

The positionable, robotically controlled probe 18 is located over a wash station (not shown). Then, with the valve between the source of pressurized water and the tubing 10 open, water is forced through the tubing 10 and probe 18, into the wash station. Additionally, the pump 22 under the control of the interface circuit 100 can be operated to withdraw water into the pump chamber. Once again, the pump 22 in a preferred embodiment is a precision diluter pump operated through the use of a stepper motor under the control of the pump control 110 and interface circuit 100.

Once the system is so primed, the water supply valve is closed. The probe 18 is then removed from the wash station, and the pump is further operated to withdraw more water backing into the pump 22 chamber. This results in the introduction of a leading air slug 122 into the probe 18 and tubing 10.

Embodiments of the presently disclosed system are employed to deliver various reagents, including but not limited to solid-phase reagents and specific allergen reagents, as well as ancillary reagents including diluents and pre-treatment solutions. After establishing the water backing as described above, the probe 18 is positioned within one such liquid to be aspirated, for example, the reagent 12 in the reagent container 20, prior to operating the pump 22 to withdraw reagent into the tubing 10.

At system initialization, a processor 200 and associated memory 202 are programmed with data related to location of reagent containers, and the total liquid capacity of each container. From that point on, the processor tracks the number of times liquid is withdrawn from each container, also referred to as the number of "shots". Knowing the starting capacity, the amount withdrawn with each aspiration, and the number of aspirations for each container, the processor is capable of indirectly determining whether it is possible to withdraw further reagent from the container, or in other words, the number of "shots" remaining. This technique is referred to as "shot-counting". If so, the processor commands the positioning of the probe 18 and the operation of the pump 110, through the interface circuit 100. In a preferred embodiment of the present invention, the probe 18 is positioned within a well at the bottom of the reagent container 20 in order to maximize the amount of reagent that can be withdrawn from the container.

In one embodiment, the interface circuit 100 is a microcontroller of limited speed and processing power. As such, the determination of whether to enable further aspiration from a container is performed by the processor 200, using the associated memory 202, thus freeing the interface circuit for other functions. Alternatively, the interface circuit 100 is provided with sufficient processing power to perform the functions of probe positioning control, threshold determining and comparison circuit 50 results processing, and pump control. A further alternative embodiment delegates the same functions to a central processor, eliminating the need for the interface circuit 100.

In the embodiment employing both the centralized processor 200 and localized interface circuit 100, the processor 200 instructs the interface circuit 100 to perform the aspiration function if the processor determines sufficient reagent remains in the reagent container, based upon initial reagent container capacity, volume aspirated by each probe aspiration, and number of such aspirations. Depending upon the needs of a particular assay, the processor may also determine whether sufficient reagent or other liquid exists in one or more remaining containers, and sequentially command the probe into those containers to withdraw further liquids into the probe and tubing.

Once all required aspirating has been completed, the processor 200 commands the elevation of the probe 18 from the last container, and operates the pump again in order to aspirate a trailing air slug 124. The system is then ready is begin a dispense cycle once the probe 18 has been positioned above a target receptacle, such as a cuvette.

As previously noted, certain faults must be guarded against, including a reagent container 20 having less reagent than expected or being empty or missing, improper positioning of the probe tip within a reagent container, a break in the tubing 10, insufficient water backing, an occlusion of the probe, tubing or pump system, a failed or failing pump 22, faulty pump or probe positioning controls, failure of the sensor 30, referencing on an air bubble before the detector, or the like. The previously described technique for timing the occurrence of the liquid-air boundaries works in embodiments having short tubing runs or relatively rigid tubing. However, a long run of flexible tubing between the diluter pump 22 and the probe tip 18 introduces variables in the total volume between those points, due to tube expansion and the compressibility of air. Thus, delays can be found between the movement of the diluter piston and the movement of the liquid column at the optical detector 30.

An alternative approach to confirming the proper aspiration and dispensation of liquids involves creating a time-based record of the signal level out of the threshold determining and comparison circuit 50, beginning at the point the trailing air slug 124 is started, at least until the liquid-air boundary of the trailing air slug 124 is expected at the optical detector 30. This record is then compared against a calibration record to determine if the liquid-air transition occurred within an expected time interval. This approach is more preferable for embodiments employing approximately 100 inches of flexible tubing between the diluter 22 and probe tip 18. Such an embodiment experiences significant delays from the initiation of diluter movement to the actual movement of the liquid column in the tubing. Since these delays are inconsistent, liquid monitoring in real-time becomes unreliable. Further, even though the total volume displaced does ultimately correlate to the diluter 22 piston movement, though not necessarily at the same speed as the piston movement, the air and tubing are compressible, making it difficult to accurately measure the volume of a slug of liquid or air in the tubing as it passes through the detector 30.

Other obstacles which are addressed through the use of the presently disclosed technique include the presence of air bubbles which tend to break into multiple, smaller bubbles which may shift their relative position in the liquid column. These bubbles may result from the break up of an intended "bubble" such as the leading air slug 122, or from bubbles introduced into the liquid column between consecutive aspirations of more than a single liquid.

The calibration record is determined through the use of the water backing system, and can be performed at system initiation, or periodically throughout an operating cycle. For instance, while the probe is being washed with deionized water flowing through the tubing, the signal output of the detector is provided to the sample and hold circuit 60 within the threshold and determining circuit 50. The output of the sample and hold circuit 60 is then used as the reference level for the comparator 80. The output of the comparator 80 is subsequently utilized by the processor 200 in recording traces for each aspirate or dispense cycle, and in determining whether an aspirate or dispense cycle fell within acceptable tolerances.

Each trace is preferably recorded using a run-length encoding technique. For instance, a particular trace may be defined as x counts at a liquid state, followed by y counts at an air state, followed by z counts at liquid again. The counts for each trace are provided by the stepper motor operating the liquid pump 22. Therefore, the sampling rate is determined by the desired speed of aspiration or dispense. In one embodiment, each step loosely correlates to 1 $\mu l$ of diluter motion. However, in an embodiment which utilizes several stepper motor half-steps for acceleration or deceleration, there is no explicit accounting for such special cases, resulting in a few extra readings at the beginning or end of each trace. This is compensated for, as described below.

If the liquid-air transition occurred within the proper time interval during aspiration, a similar record is maintained during a subsequent liquid dispense cycle. Here, the record is maintained from before the occurrence of the air-liquid transition at the optical detector until the dispense cycle is complete. For instance, the dispense record can be initiated at the start of the dispense cycle. Then, a subsequent analysis of the dispense record reveals whether the optical detector 30 reported a liquid state from the occurrence of the air-liquid transition of the trailing air slug 124 through the end of the dispense cycle, with the exception being for the possible occurrence of a leading air slug 122.

Following each aspirate or dispense cycle, the processor 200, executing host software stored in memory 202, reads back the trace from the completed cycle for comparison against a reference trace. For proper reagent aspiration, there should be a liquid-to-air transition seen in the trace for the trailing air gap aspiration at a location correlating to internal tubing volume between the probe tip and the detector.

This places the following requirements on aspiration/dispense sequences according to the present disclosure. First, each sequence must include the aspiration of, or must be proceeded by the aspiration of, a trailing air slug 124. Second, the trailing air gap must be aspirated at a consistent speed. Third, the trailing air gap must be of a sufficient volume to move the end of the liquid column past the detector 30, such that a sufficient volume of air following the liquid-air transition of the trailing air slug 124 is easily distinguishable from any other air volume, including the leading air gap.

Figure 9A:
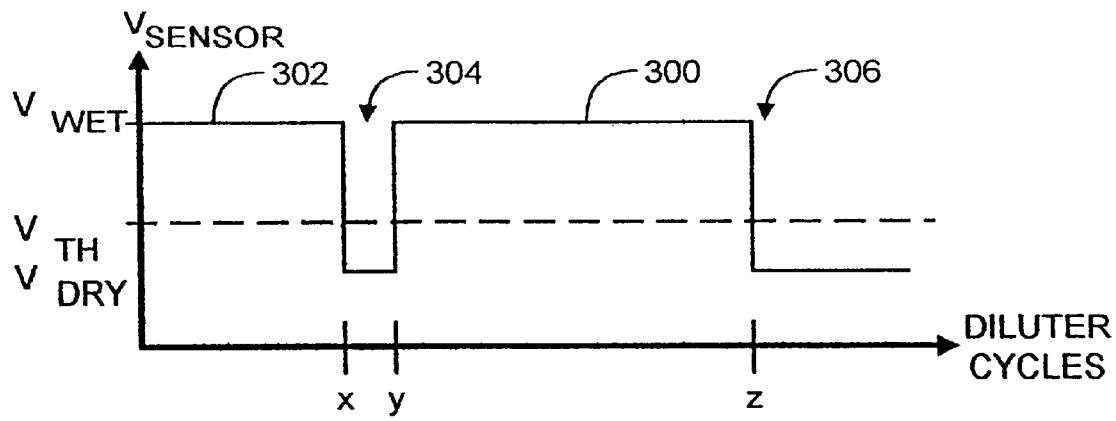
FIGS. 9A, 9B and 9C are graphs illustrating the timing of signals employed in monitoring aspirating functions for the apparatus of FIG. 8.
Figure 9B:
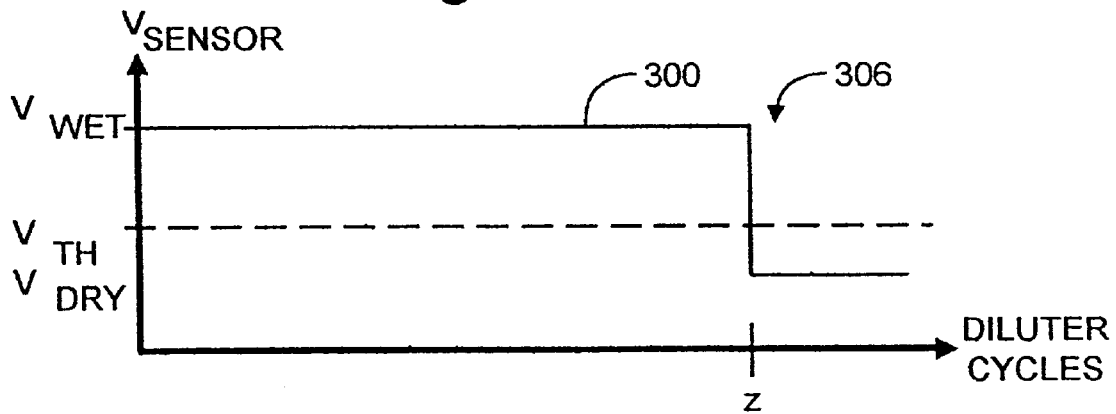

FIGS. 9A and 9B illustrate traces for typical aspiration cycles. In FIG. 9A, the reagent aspiration 300 is relatively small, such that the water backing 302 is before the detector initially. After x stepper motor cycles, the leading air slug 304 is detected, which persists until occurrence of y stepper motor cycles. At that point, the reagent itself 300 is before the detector. Then, at z stepper motor cycles, the liquid-air transition of the trailing air slug 306 is detected. This trace is more typical for a single reagent aspiration, as compared to a multiple reagent aspiration of greater cumulative reagent volume.

In FIG. 9B, the reagent aspiration 300 is large enough, such that at the commencement of the trailing air slug 306 aspiration, the leading air slug has already passed upstream of the detector such that the leading air slug does not appear in this aspiration trace.

Each of these traces is then compared against a calibration trace made using the water backing priming cycle. The liquid-air transition is measured in terms of stepper motor cycles and is recorded as the reference edge location for the actual reagent aspirations.

The location of the trailing air slug 306 for the trailing air slug is compared to that of the calibration trace. If the edge is in the same location, within acceptable error limits, it is assumed that the proper volume was aspirated.

Figure 9C:
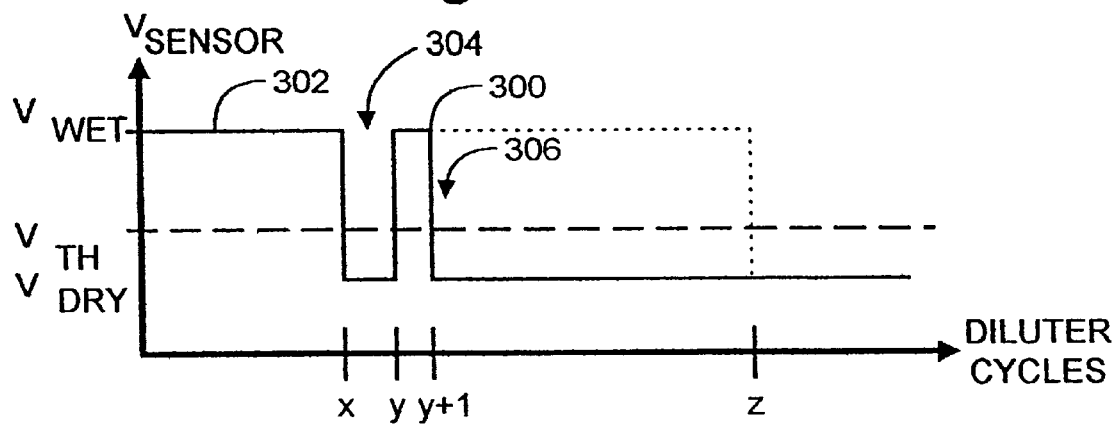

FIG. 9C illustrates a trace generated by a "short shot" aspiration. The leading air slug 304 may or may not be visible, depending upon the volume of reagent aspirated. In FIG. 9C, this volume is relatively small, such that the water backing 302 is before the detector at the initiation of the trace (i.e. at the beginning of the aspiration of the trailing air slug 306). At the end of the leading air slug 304, the reagent 300 is detected, as expected. However, the liquid-to-air transition of the trailing air slug 306 is expected, within a given tolerance, after z stepper motor cycles. As illustrated, it occurred only one stepper motor cycle after the start of reagent aspiration. This error condition would then be reported by the processor 200.

Once the aspiration cycle has been accepted by the processor, the liquid-air boundary of the trailing air slug 306 can then be utilized in confirming the total volume dispensed, again within acceptable tolerances. The dispense trace will ideally be only in a liquid, reagent 300 state at the detector from the air-to-liquid transition between the trailing air slug 306 and the reagent 300 to the end of the dispense cycle, with the exception of the leading air slug 304, if any. For instance, in FIG. 10A, the trailing air slug 306 is evident before the detector until the air-to-liquid transition of the reagent 300. The fluid state is then observed by the detector until the end of the dispense cycle, with the exception of the leading air slug 304.

Figure 10A:
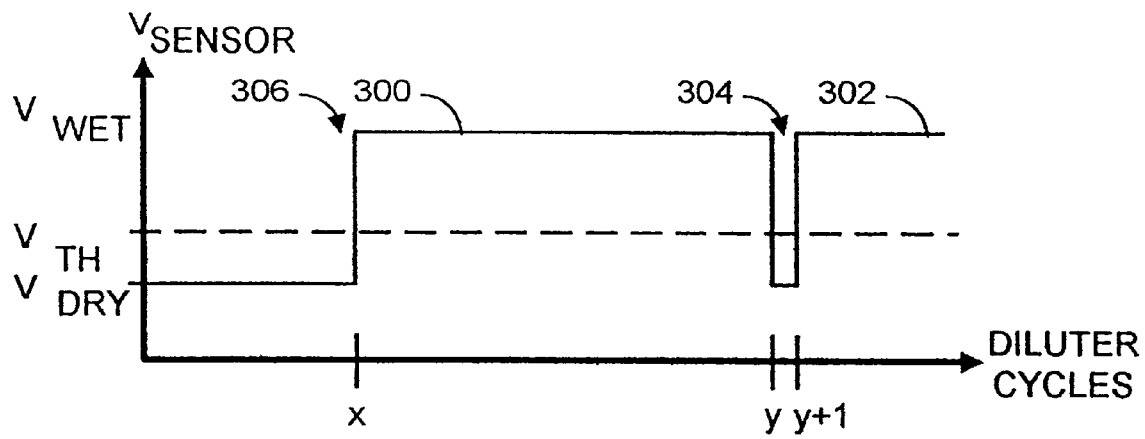
FIGS. 10A and 10B are graphs illustrating the timing of signals employed in monitoring dispensing functions for the apparatus of FIG. 8.

Another way of characterizing the analysis performed by the processor 200 is that the number of air detections between the air-to-liquid transition, the trailing air slug 306 and reagent volume 300 border, and the end of the dispense cycle is compared against an acceptable threshold. In FIG. 10A, the only air detections would be that of the leading air slug 304, which would be below a threshold number of air detections. In FIG. 1OB, however, a number of additional air detections 308 are recorded, which may be the result of air bubbles in the originally aspirated volume. Thus, even though the volume originally aspirated appeared to be correct, the trace of the dispense cycle reveals that the volume aspirated was discontinuous, and an error should be reported by the processor 200 or interface circuitry 100.

Figure 10B:
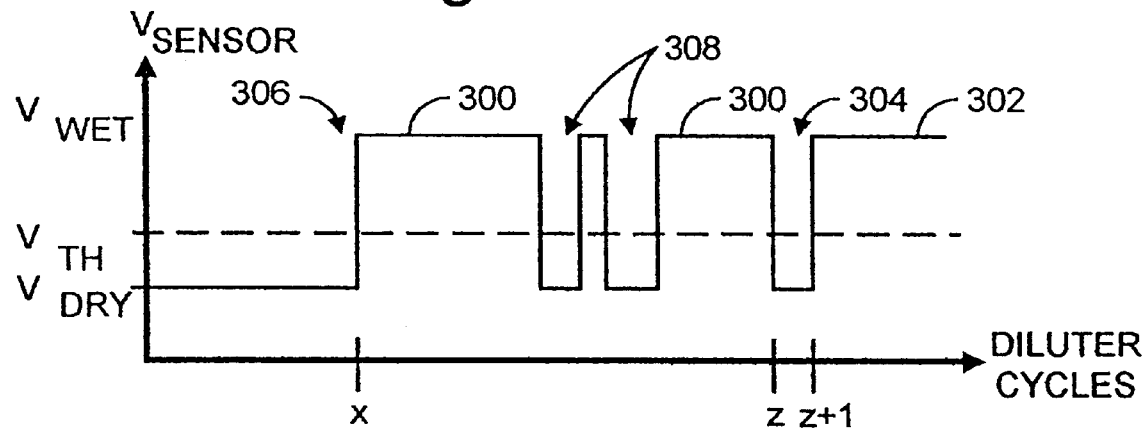

The trace of FIG. 10B could occur, for instance, if this were a dual reagent aspiration of 250 $\mu$l followed by 50 $\mu$l, though the source of the 250 $\mu$l only contained 175 $\mu$l.

Software used for analyzing the signal traces includes a number of variables used to adjust the sensitivity of the volume error detection. This is necessary since trace counts do not correlate directly to aspirate volumes, nor do leading and trailing air slugs maintain their integrity. For example, an aspiration of 10 $\mu$l leading air slug 304 followed by 70 $\mu$l of reagent 300 (see FIG. 9A) may result in a dispense trace of 32 counts of air, one count of liquid, 23 counts of air, 30 counts of liquid, one count of air, 36 counts of liquid, four counts of air, and 94 counts of liquid. The initial 32+23 counts of air represent the trailing air gap 306 of FIG. 10A, divided by a liquid droplet. The reagent 300 is then represented by the 30+36 counts of liquid, divided by a one count air bubble. This is followed by the leading air gap of four counts, and then the water backing.

It is thus necessary to define a filtering technique involving a window that can be slid along the reported trace. For instance, assume the processor is looking for the liquid-to-air boundary of a trailing air slug upon aspiration. A 25 count window can be defined such that 15 or 25 counts following a "liquid" count at the detector is defined as a valid liquid-to-air transition. This is preferred over defining a valid air-to-liquid transition as a "liquid" count followed by 15 air counts, since it is likely that the air gap will be split by at least one liquid droplet.

Likewise, the air-to-liquid transition on dispense can be identified using such a window. Once so identified, the number of air counts must not exceed a predetermined threshold in order for the trace to be confirmed as valid by the processor.

The processor of one embodiment responds to a failed aspiration trace by commanding the recalibration, or re-priming, of the system. In fact, this recalibration upon failure may be repeated a number of times prior to reporting a failure.

Figure 11A:
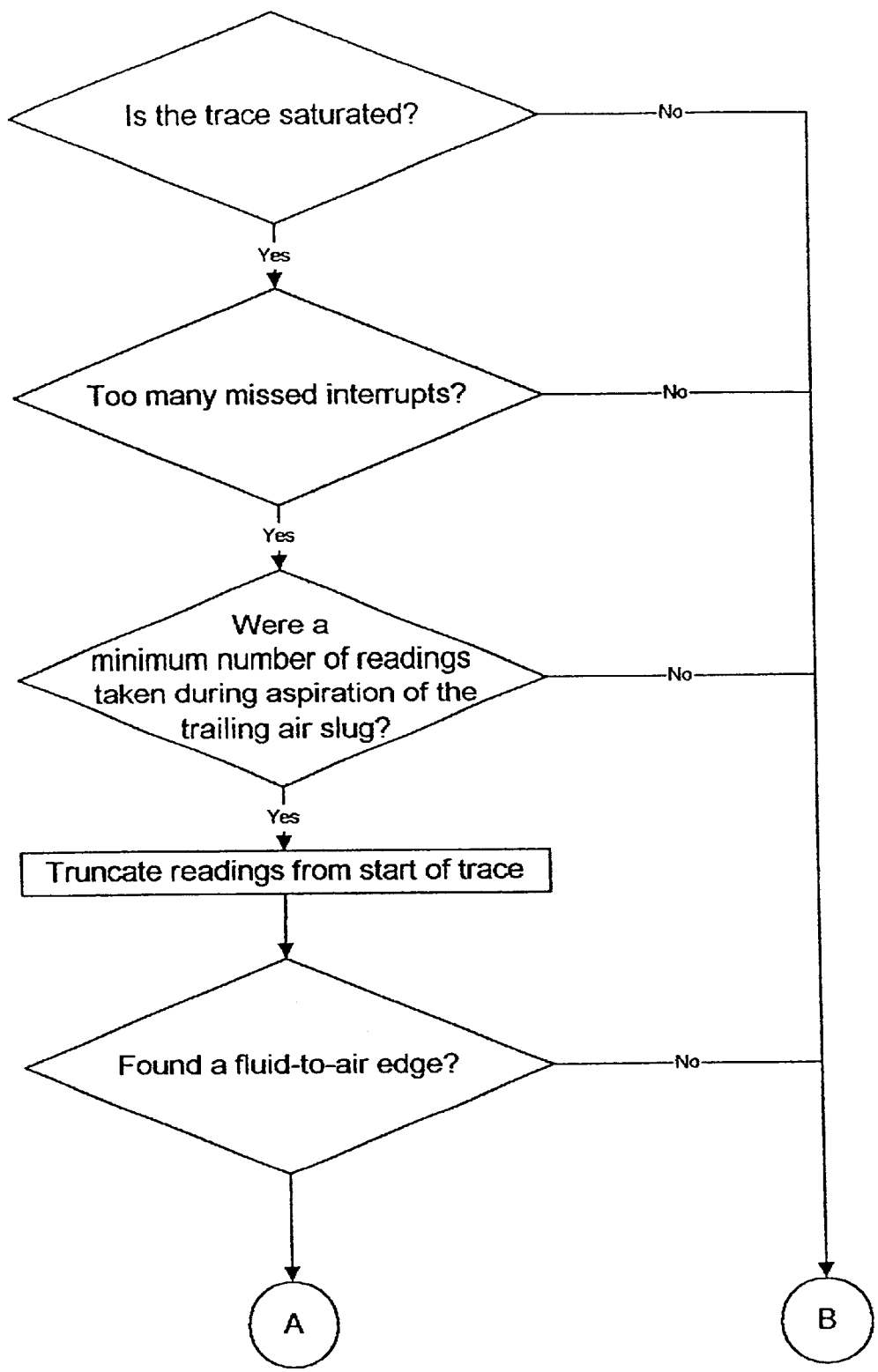
FIGS. 11 and 11B are flow charts illustrating a procedure for evaluating the aspiration of a trailing air slug according to the present invention.
Figure 11B:
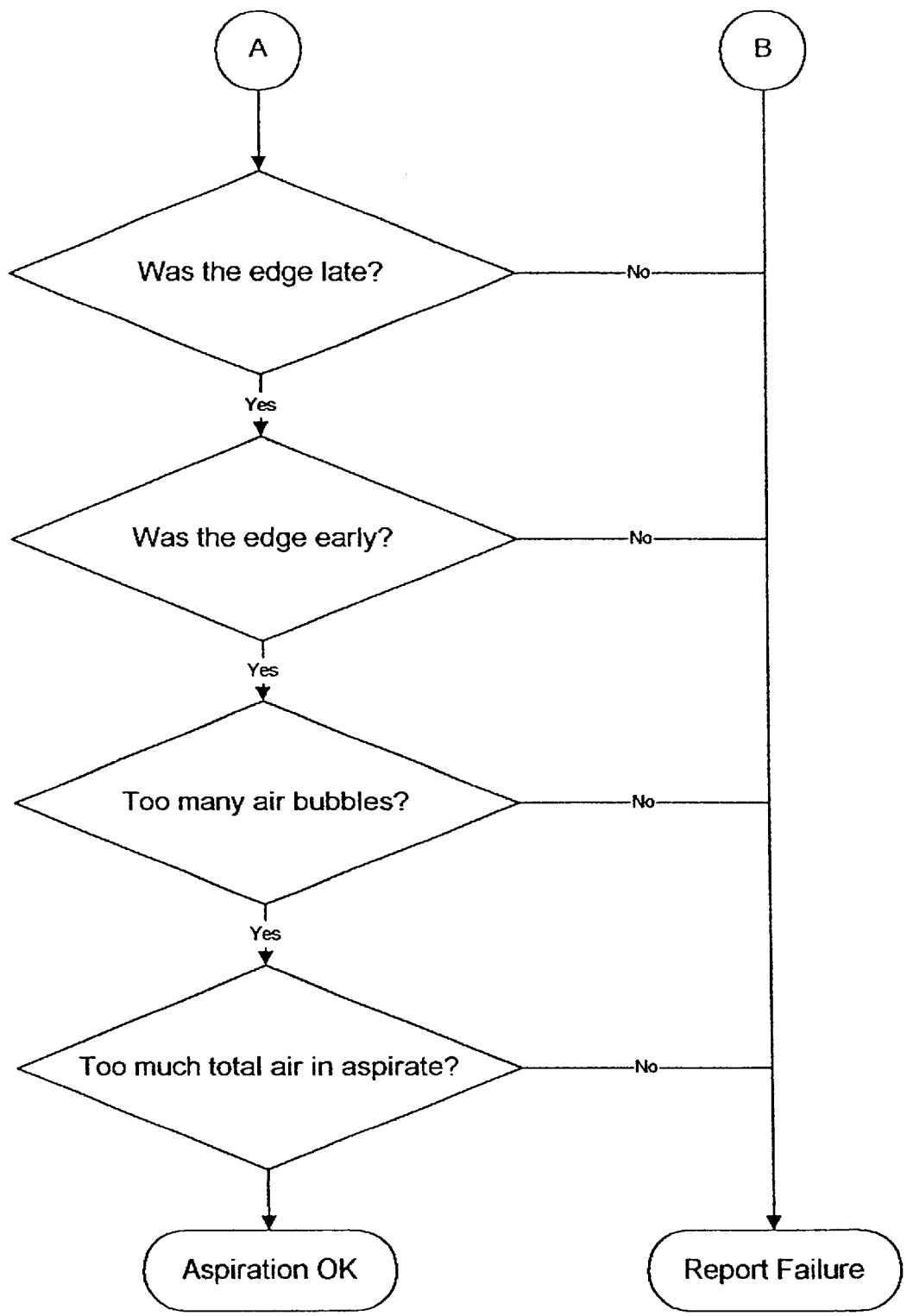

A typical evaluation sequence of an aspiration cycle by the processor 200 is illustrated in FIGS. 11A and 11B. The first step is for the processor to determine if more than a maximum number of liquid-to-air-to-liquid transitions occurred. One embodiment of the hardware of the present system cannot accurately record transitions if they occur too rapidly or are too many in number. This may be an indication of a very bubbly liquid column.

A further step taken during the evaluation of an aspiration trace involves determining whether a number of missed interrupts exceeds a maximum value stored in the memory 202. The detector signal, from the threshold determining and comparison circuit 50, is conveyed to the processor 200 as a timed interrupt that operates in the background during trailing air slug aspiration and dispense. As such, the interrupt is given lower priority than, for instance, motor control or communication between the interface circuit. Thus, it is possible that such interrupts can be missed. It is acceptable to miss some readings since the sampling signal does not need to be extremely accurate. However, a defined threshold ensures that an excessive number of interrupts are not reached, leading to gross inaccuracies in the trace to be evaluated.

As noted above, the diluter motor is ramped at the beginning and end of each movement, resulting a small number of excess readings at the detector. The software or firmware for the processor compensates for this by adding a number of liquid readings to the expected number, and also defines a tolerance number above and below the expected number of readings. This is reflected in FIG. 11A by the step determining whether a minimum number of readings were taken during the aspiration cycle.

Since there is likely to be a lag in liquid column movement after initiation of diluter pump action, a prescribed number of readings are truncated from the beginning of the trace.

Also as previously noted, small volume reagent aspirations may result in the appearance of the leading air slug 122 in the trace, along with the desired trailing air slug 124. It is thus necessary to distinguish between the two. The leading air slug 122 is considerably smaller in volume than the trailing air slug. However, the time delay in liquid column movement may make the leading air slug appear to be larger than it actually is. Tighter tolerances on the definition of the trailing air slug is thus preferable in order to identify the liquid-to-air edge of the trailing air slug.

In order to address a possible error condition where more liquid is aspirated than is required, and consequently the liquid-to-air edge at the trailing air gap is late, an upper end tolerance is defined for the occurrence of the liquid-to-air boundary of the trailing air slug during aspiration (FIG. 11B). Similarly, a tolerance on the lower end for aspirated volumes is defined to identify short shot aspirations (i.e. was the liquid-to-air edge early?).

Another limitation which is defined in software for the evaluation of the processor in a preferred embodiment is a maximum number of liquid-to-air and air-to-liquid transitions, or in other words, a maximum bubble count. An excessive number of air bubbles may indicate a poorly primed liquid system or the case in which the last, partial shot from a reagent container has been aspirated.

A limit on the total number of "air" counts detected during aspiration of the reagent is defined in a further embodiment. This can be defined through the use of a multiplier for the leading air slug volume. For instance, the software may define a multiplier of 1.5. Given a typical leading air slug volume of 10 $\mu$l, the limit would be 15 counts of air in the aspirated reagent.

If all of these conditions are successfully met, it is assumed that the proper volume of liquid was aspirated during the aspiration cycle.

Figure 12A:
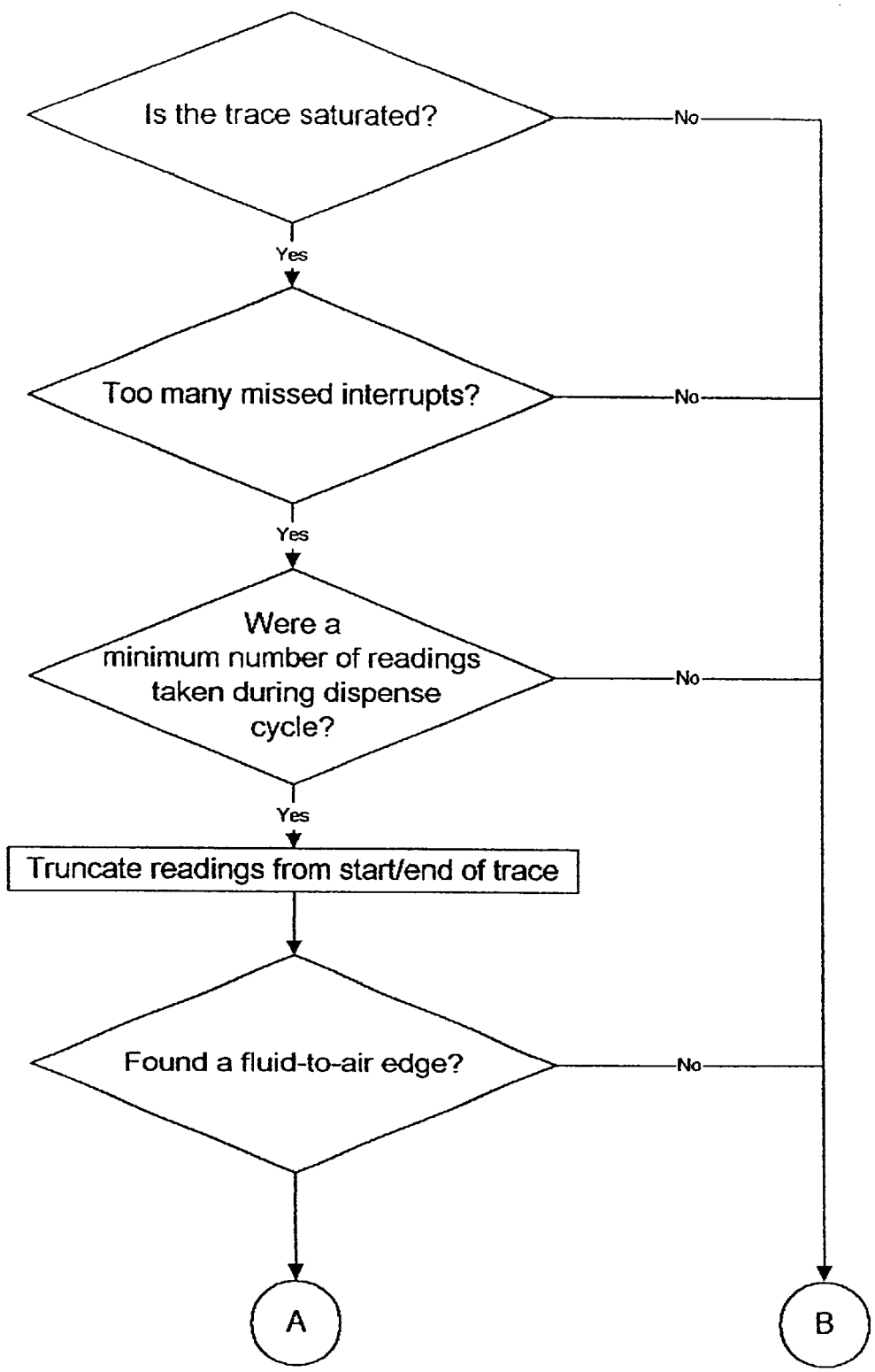
FIGS. 12A and 12B are flow charts illustrating a procedure for evaluating the dispense of an aspirated volume according to the present invention.
Figure 12B:
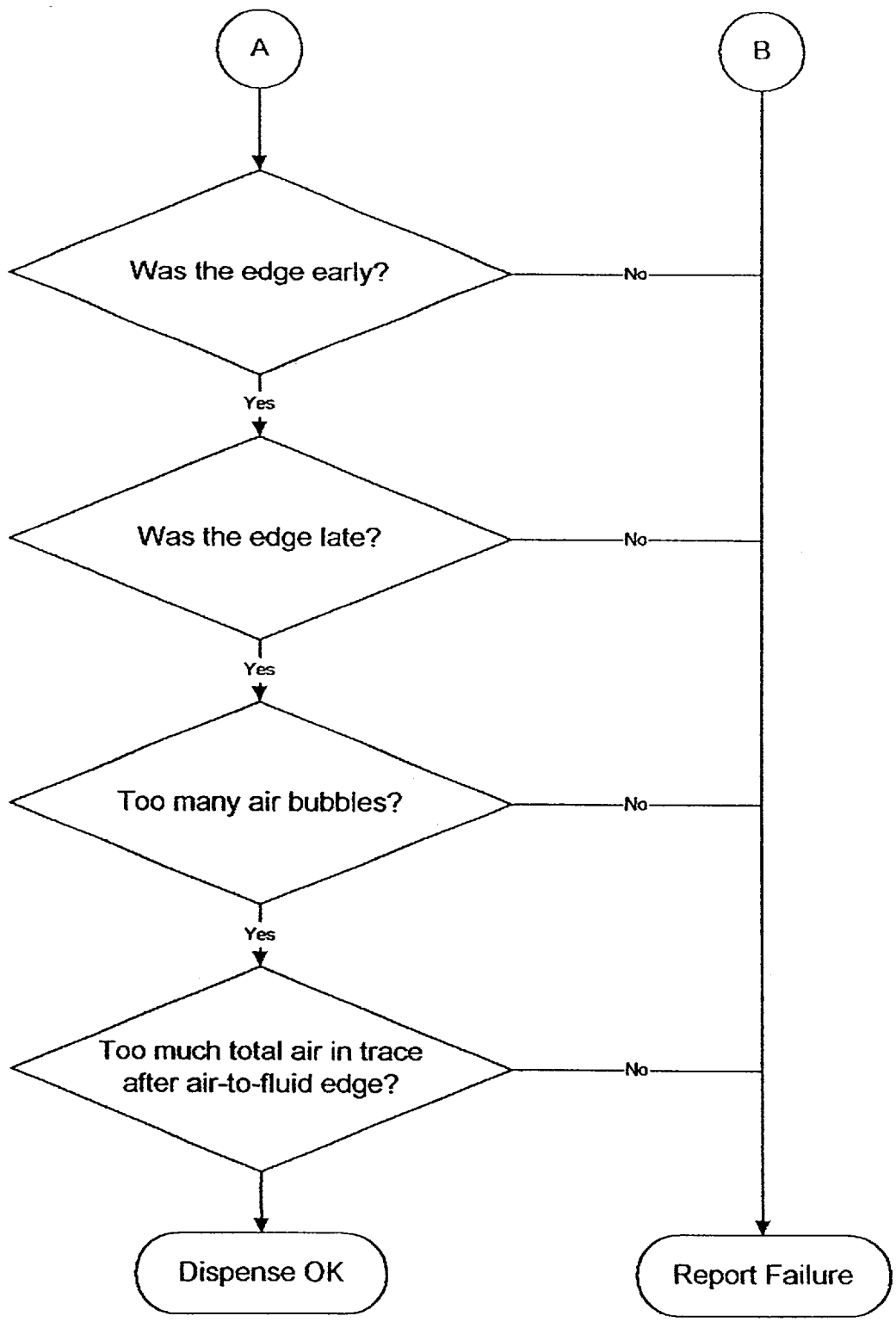

A similar set of limitations and thresholds are employed for the dispense cycle traces, as shown in FIGS. 12A and 12B. The total number of air-to-liquid-to-air transitions are accumulated and compared against a maximum number in order to determine whether the dispense trace is saturated, or in other words, whether the frequency of transitions exceeded the capacity of the processor to evaluate.

The number of missed interrupts, as described above are compared against a maximum threshold in order to evaluate whether the recorded dispense trace is an accurate reflection of the pump cycle. The processor 200 adds counts in order to compensate for pump acceleration and deceleration, then compares the total count against a target number, given a specified tolerance.

Next, counts from the start of the trace are deleted to compensate for delay in liquid column response to diluter movement, as described above with respect to the aspiration cycle. Likewise, the processor also identifies a number of counts to truncate at the end of a trace due to the water backing (which is of no interest).

After these adjustments, a determination is made as to whether an air-to-liquid edge has been identified. This should be quite predictable, since it will closely correspond with the liquid-to-air edge of the trailing air slug on aspiration. Once identified, a window of appropriate size is utilized in evaluating whether the edge occurred (FIG. 11B) too early or too late.

Next, a determination is made whether the maximum number of bubbles in the dispense, after the liquid-to-air transition at the reagent volume, is exceeded. Finally, having identified the air-to-liquid edge of the trailing air slug and having established that it occurred at the proper point in the trace, the processor determines whether the previously aspirated volume does not contain excessive air. This is achieved by comparing the trace against a maximum number of "air" counts after commencement of the reagent volume detection, keeping in mind possible small volumes of air due to the trailing air slug.

These and other examples of the invention illustrated above are intended by way of example and the actual scope of the invention is to be determined from the following claims.

What is claimed is:

1. A method for validating the performance of a pump system comprising a controller, a pump, a fluid-conveying pathway, a reservoir of reference liquid, and a detector adjacent said pathway, said method comprising:

operating said pump, by said controller, to dispense a quantity of reference liquid from said reservoir wherein said reference liquid fills said pathway;

operating said pump, by said controller, to aspirate a first quantity of air, subsequent to said dispensing of said quantity of reference liquid, until said detector detects a leading edge of said first quantity of air;

detecting, by said detector, the presence of reference liquid or said first quantity of air in said pathway at known intervals;

recording results of said step of detecting the presence of reference liquid or said first quantity of air as a reference data set by said controller;

using said reference data set, by said controller, to define a set of acceptable intervals;

operating said pump, by said controller, to aspirate a quantity of sample liquid into said pathway;

operating said pump, by said controller, to aspirate a second quantity of air into said pathway following said quantity of sample liquid;

detecting, by said detector and at said known intervals, the presence of said second quantity of air or said sample liquid in said pathway;

identifying, by said controller, an interval at which said second quantity of air was first detected by said detector following said quantity of sample liquid; and determining, by said controller, if said interval at which said second quantity of air was first detected is within said set of acceptable intervals.

2. The method of claim 1, further comprising:

operating said pump, by said controller, to dispense at least a portion of said quantity of sample liquid; and determining, by said controller, if said detector detected said sample liquid at an acceptable number of intervals during said pump dispense operation.

3. The method of claim 1, wherein said known intervals are correlated to the operation of said pump.

4. The method of claim 3, wherein said steps of operating of said pump comprise operating a stepper motor associated with said pump.

5. The method of claim 4, wherein said known intervals are cycles or sub-cycles of said stepper motor.

6. The method of claim 1, further comprising:

operating said pump, by said controller, to dispense at least a portion of said quantity of sample liquid; and determining, by said controller, if said detector detected air for no more than a maximum number of intervals during said pump dispense operation.

* * * * *

UNITED STATES PATENT AND TRADEMARK OFFICE
CERTIFICATE OF CORRECTION

PATENT NO.   : 6,250,130 B1  
DATED        : June 26, 2001  
INVENTOR(S)  : David J. Howard et al.

It is certified that error appears in the above-identified patent and that said Letters Patent is hereby corrected as shown below:

<u>Column 11,</u>  
Line 24, "fluid" should read -- liquid --; and  
Line 34, "1OB," should read -- 10B, --.

Signed and Sealed this

Twentieth Day of August, 2002

Attest:

JAMES E. ROGAN  
Attesting Officer   Director of the United States Patent and Trademark Office